United States Patent [19]

Steffel et al.

[11] 4,326,535

[45] Apr. 27, 1982

[54] CIRCUIT AND METHOD FOR THE RADIOTELEMETRY OF ESOPHAGEAL PH IN AN ECG RADIOTELEMETRY SYSTEM

[75] Inventors: Charles R. Steffel, Munroe Falls; Bruce C. Taylor, Kent, both of Ohio

[73] Assignee: Akron City Hospital, Akron, Ohio

[21] Appl. No.: 149,427

[22] Filed: May 13, 1980

[51] Int. Cl.³ .............................................. A61B 5/00
[52] U.S. Cl. .................................... 128/631; 128/903
[58] Field of Search ........ 128/903, 631, 635, 670–671, 128/696, 700

[56] References Cited

PUBLICATIONS

Kurt, E.J. et al, "Radiotelemetry pH Determination for Gastroesophageal Reflux," Amer. Jrnl. Gastroenterology vol. 58, pp. 390–395 (1972).
Maycock, B. F., "A Long—Term Remote Intragastric pH and Motility Monitoring System," Biomed. Sci. Instr., 6th Nat. Symp., May 21-23, 1968, pp. 127–135.
Baurschmidt, P. et al., "Implant. Telem. System for Long—Term pH Monitoring in the Stomach," Biotelem. 2nd Int. Symp., Davos, Switz., 1974 pp. 46–48.
Briskman, B., "Telemetry Today, " Electronics Sep. 6, 1973, pp. 31–37.
Filshie, J. H., "A Hybrid Thin—Film Multichannel Biotelem. Transmitter, " Conf. on Hybrid Microelectro., Loughborough, Eng. 9–11 Sep. 1975 pp. 49–56.

Primary Examiner—Robert W. Michell
Assistant Examiner—Francis J. Jaworski
Attorney, Agent, or Firm—Hamilton, Renner & Kenner

[57] ABSTRACT

A circuit and method for radiotelemetry of an esophageal pH signal in an electrocardiogram (ECG) signal radiotelemetry system includes esophageal and reference pH electrodes (16 and 17) connected to a pH meter (15) for monitoring esophageal pH and generating a signal proportional thereto and a waveform converter circuit (12) for converting the same to a signal whose waveform is similar to an ECG waveform and one of whose parameters, such as frequency, is proportional to esophageal pH. A conventional ECG radiotelemetry system (13) includes an ECG signal transmitter (31) receiving and broadcasting the converted signal to a remote ECG signal receiver (32). A display (14) receives the demodulated converted waveform from ECG signal receiver (32) and displays indicia of esophageal pH.

12 Claims, 5 Drawing Figures

CIRCUIT AND METHOD FOR THE RADIOTELEMETRY OF ESOPHAGEAL PH IN AN ECG RADIOTELEMETRY SYSTEM

TECHNICAL FIELD

The present invention relates generally to a device for the diagnosis of gastroesophageal disorders, such as inflammatory disease or lower esophageal sphincter incompetence, by the monitoring of esophageal pH. More particularly, the present invention relates to a circuit and method for the radiotelemetry of esophageal pH data useful in the evaluation of gastroesophageal disease.

BACKGROUND ART

It has long been established that the continuous monitoring of pH in the distal esophagus over extended periods of time (i.e., of at least 24 hours) provides data useful in the evaluation of gastroesophageal disease. The earlier devices developed to perform such monitoring employed an electrode inserted through the nasal passage into the esophagus, a reference electrode in contact with the patient's skin, an electrical shock isolation module through which the signal from the electrodes and the patient were electrically isolated from monitoring instruments, and a pH meter and recording apparatus receiving, displaying and recording the isolated signal.

These devices effectively tether the patient to the pH meter and recorder because the electrodes and pH meter must be wired together by electrical conductors. With such a restricted range of movement, the patient's activities must be similarly circumscribed, resulting in data, generally known as a reflux pattern, that is not usually a true reflection of what generally occurs during the patient's ordinary activities.

More recently another device has been employed in the monitoring of pH in the distal esophagus. This device envisions the patient swallowing a capsule containing both a pH electrode and a micro-miniature radio transmitter having its own self-contained power supply adequate for up to an eight hour monitoring period. The capsule would be positioned and secured in the gastric pouch at the esophagogastric junction by string tied to the capsule and taped to the incisor teeth. A belt containing a plurality of pick-up antennas was wrapped around the patient's waist and electrically connected via conductors to the necessary instrumentation. In this manner the pH data could be radiotelemetered to the pick-up antennas and associated instruments.

For several reasons this more recent device is at least as deleterious as those which preceded it. The patient is subjected to even greater discomfort as a result of utilization of the capsule system. The antenna belt, which must be physically connected to the instrumentation, subjects the patient to at least as much interference to and limitation upon his zone of movement as that of the earlier devices, and still creates a possibility of electrical shock. The limited power capacity of the capsule's self-contained power supply results in monitoring times restricted to periods too short to provide an adequate sampling of the patient's reflux pattern. Moreover, the necessity for highly specialized equipment makes the system relatively expensive to purchase and operate, requiring the constant supervision of trained personnel, which supervision may only be provided by hospitalization for the duration of the study.

DISCLOSURE OF INVENTION

It is, therefore, an object of the invention to provide an economical circuit and method for the radiotelemetry of esophageal pH without restricting the patient's mobility to the immediate vicinity adjacent the instrumentation, thereby significantly improving the reliability of the reflux pattern obtained thereby.

It is another object of the invention to provide a circuit and method for the radiotelemetry of esophageal pH, as above, without significant discomfort and hazard of shock.

It is still another object of the invention to provide a circuit and method for the radiotelemetry of esophageal pH, as above, that has a continuous operational period of at least several days.

It is yet another object of the invention to provide a circuit and method for the radiotelemetry of esophageal pH, as above, in which extensive use is made of existing, widely available ECG radiotelemetry systems, thereby significantly reducing the initial cost of esophageal pH monitoring devices.

It is a further object of the invention to provide a circuit and method for the radiotelemetry of esophageal pH, as above, in which the device may be operated by the patient and esophageal pH studies performed on an outpatient basis, thereby significantly reducing the operational cost of such tests.

These and other objects of the present invention over existing prior art forms will become more apparent and fully understood from the following description in conjunction with the accompanying drawings.

In general a circuit for radiotelemetry of an esophageal pH signal in an electrocardiogram (ECG) signal radiotelemetry system includes means for monitoring esophageal pH and generating a signal proportional thereto, waveform converter means for receiving the signal from the means for monitoring esophageal pH and converting the same to a signal whose waveform is similar to an ECG waveform and one of whose electrical parameters is proportional to esophageal pH, transmitter means for receiving the converted signal from the waveform converter means and broadcasting the same upon a radio frequency carrier, receiver and demodulator means for receiving the broadcast signal and demodulating the same to obtain the converted signal similar to an ECG waveform, and display means receiving the demodulated converted signal whose waveform is similar to an ECG waveform and displaying indicia of the esophageal pH.

A method for radiotelemetry of an esophageal pH signal in an electrocardiogram (ECG) signal radiotelemetry system includes the steps of monitoring esophageal pH including the step of generating a signal proportional to the instaneously measured esophageal pH, converting the signal proportional to the instantaneously measured esophageal pH to a signal whose waveform is similar to an ECG waveform and one of whose electrical parameters is proportional to esophageal pH, broadcasting said converted signal upon a radio frequency carrier, receiving and demodulating the broadcast signal to obtain the converted signal whose waveform is similar to an ECG waveform, and, displaying indicia of the instantaneous esophageal pH.

PREFERRED EMBODIMENT FOR CARRYING OUT THE INVENTION

Figure 1:
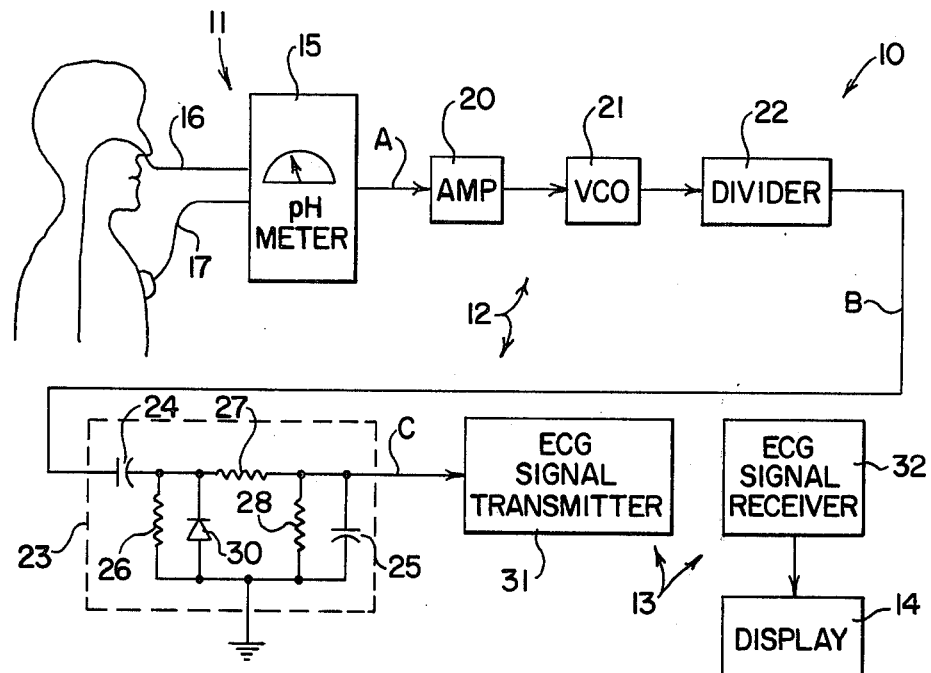
FIG. 1 is a block diagram of an exemplary circuit according to the concept of the present invention in which a portion thereof is depicted schematically.
Figure 2:
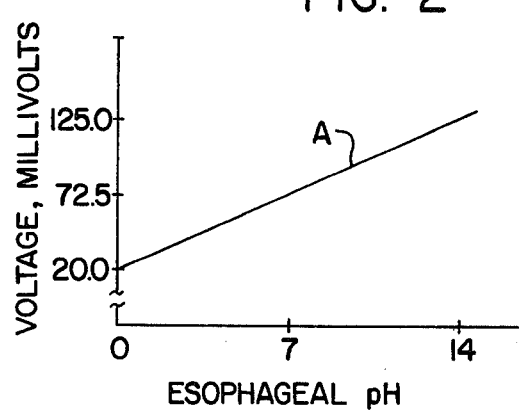
FIG. 2 is a graph of an exemplary analog voltage output from the pH meter as a function of esophageal pH.

FIG. 1 illustrates a circuit generally indicated by the numeral 10, which also embodies a method, for radiotelemetry of an esophageal pH signal in an electrocardiogram (hereinafter referred to as "ECG") signal radiotelemetry system. Circuit 10 broadly includes pH monitoring device 11, waveform converter circuit 12, ECG signal radiotelemetry system 13, and display 14.

pH monitoring device 11 may include any conventional pH meter 15, esophageal pH electrode 16 and reference pH electrode 17. For maximum patient mobility, it is greatly preferred to employ a lightweight, battery powered portable pH meter providing a D.C. signal output whose voltage magnitude is directly proportional to the instantaneously measured esophageal pH. FIG. 2 is a graph of an analog voltage output from an exemplary pH meter 15 where the incremental voltage change is approximately 7.5 millivolts per pH unit and a 20 millivolt D.C. offset is provided at a pH of 0. Esophageal pH electrode 16 may be a two millimeter diameter glass electrode and is usually inserted through the patient's nasal passage into the esophagus and then positioned approximately five centimeters proximal to the lower esophageal high-pressure zone. Reference pH electrode 17 may be any suitable callibration electrode, such as the standard silver/silver chloride electrode utilized with electrocardiographs for attachment to the patient's skin.

Figure 3:
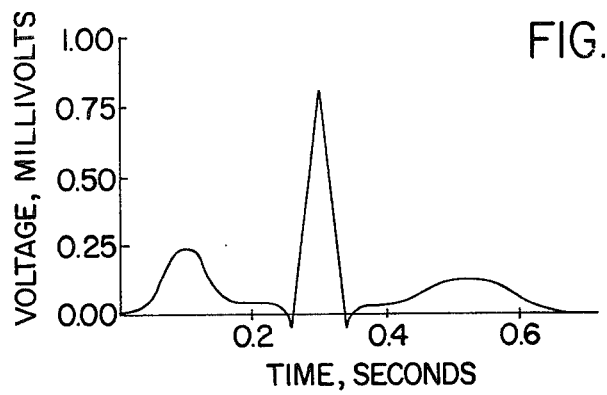
FIG. 3 is an exemplary ECG waveform illustrating the time-variant voltages produced by the myocardium during the cardiac cycle.

Waveform converter circuit 12 converts the D.C. output signal from pH meter 15 into a waveform similar to that of an ECG signal for transmission by a conventional ECG radiotelemetry system. In making this conversion at least one electrical property of the converted waveform must remain proportional to the instantaneous esophageal pH. The ECG waveform, as shown in FIG. 3 herein and discussed more fully in Section 6.1 of the text *Biomedical Instrumentation and Measurements* by Cromwell, et al., usually includes in each cycle a single somewhat triangular shaped voltage pulse of three to four times the maximum amplitude of all other voltages. This pulse is well-suited for use as a time marker in frequency measurement. Accordingly, it has been found most convenient to design waveform converter circuit 12 to convert to D.C. output signal from pH meter 15 into a waveform similar to that of an ECG signal in which the frequency of the above-noted dominant voltage pulse is proportional to the voltage magnitude of the D.C. output signal from pH meter 15. When adopting this approach, waveform converter circuit 12 may be implemented with an amplifier 20 (where necessary), a voltage controlled oscillator 21 (hereinafter referred to as "VCO"), divider 22 and waveshaping filter 23.

Where the amplitude of the D.C. output signal from pH meter 15 is inadequate for further processing, or further signal isolation is desired, a conventional amplifier 20 may be provided to receive and amplify this signal. Additionally, where expedient for compatibility purposes, amplifier 20 may include a voltage transposition circuit (not shown) such as a conventional voltage divider to shift the D.C. voltage magnitude of the D.C. output signal from pH meter 15.

Figure 4:
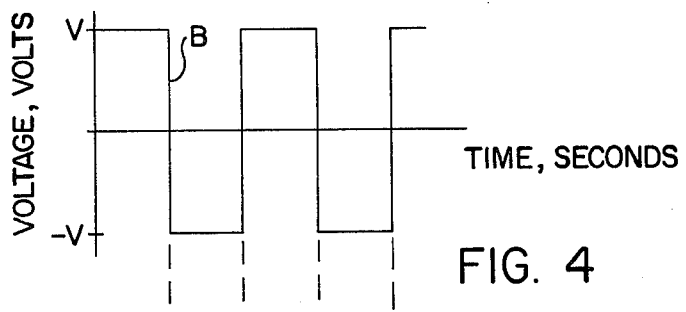
FIG. 4 is an exemplary output voltage waveform from the pH meter for an arbitrarily selected pH, and although in time coordination with the waveform in FIG. 5, is not otherwise necessarily to scale, or coordinated in time with the waveforms of FIGS. 3 and 5 or the graph of FIG. 2.

VCO 21 may be any conventional VCO that generates a square-wave output signal whose frequency is a function of the voltage magnitude of its input signal. For greater precision, a high frequency (1000 Hz or greater) VCO may be employed herein. VCO 21 receives the amplified D.C. instantaneous esophageal pH signal from amplifier 21 and therefore generates a square-wave output, depicted as waveform B in FIG. 4, whose frequency is proportional to esophageal pH.

Many ECG radiotelemetry systems are designed to process signals having frequencies on the order of magnitude of the human heartbeat, say about 1.33 Hz or 80 beats per minute (hereinafter abbreviated "bpm"). Dependent upon the frequency of VCO 21 it may be necessary to employ a conventional divider 22 to reduce the output frequency from VCO 21 to that compatable with ECG radiotelemetry system 13. Divider 22 may also be selected in conjunction with the frequency range of VCO 21 so that a preselected frequency is representative of a neutral pH of 7.0 with a linear excursion therethrough. In the above example, by selecting VCO 21 to generate a frequency of approximately 1150 Hz when its voltage input corresponds to that obtained when the esophageal pH is 7.0, and by utilizing a 14 stage ripple-carry binary counter to divide that output by $2^{13}$ (i.e., 8192), ECG radiotelemetry system 13 will receive a signal having approximately 20 bpm for each pH unit, or 140 bpm when the instantaneous esophageal pH is 7.0.

Square-wave output signal B is received by waveshaping filter 23 which includes capacitors 24, 25, resistors 26, 27, 28, and diode 30. Capacitor 24 has one end connected to one end of resistors 26 and 27 and the cathode of diode 30. The end of resistor 26 opposite that connected to capacitor 24, the anode of diode 30, and one end of resistor 28 and capacitor 25 are all connected to the system ground. The end of resistor 27 opposite that connected to capacitor 24, and the end of resistor 28 and capacitor 25 opposite that connected to ground are all connected together to form the output terminal of waveshaping filter circuit 23. Capacitor 24 and resistor 26 form an R-C circuit which produces a voltage spike with each change in square-wave output B. Diode 30 eliminates the negative-going voltage spikes, and resistor 27 insures separation of the input and output for waveshaping filter circuit 23. Resistor 28 and capacitor 25 filter and further define the remaining positive-going voltage spikes. The output waveform from waveshaping filter circuit 23 is depicted in FIG. 5 as waveform C.

Figure 5:
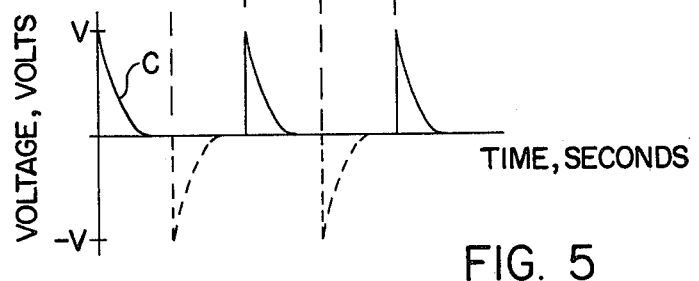
FIG. 5 is an exemplary converted output voltage waveform suitable for transmission over an ECG radiotelemetry system, and, although in time coordination with the waveform in FIG. 4, is not otherwise necessarily to scale, or coordinated in time with the waveforms of FIGS. 3 and 5 or the graph of FIG. 2.

The negative-going voltage spikes blocked by diode 30 are shown in FIG. 5 in phantom.

ECG radiotelemetry system 13 may be any conventional ECG radiotelemetry system 13 such as that designated as Model No. 78100A manufactured by Hewlett-Packard Co. of Palo Alto, California. These systems include portable, lightweight transmitters 31 and separate receivers 32 both of which are particularly adapted to radiotelemeter ECG signals. ECG signal transmitter 31 receives the output signal (waveform C) from wave-shaping filter circuit 23 and broadcasts the same to ECG signal receiver 32 which demodulates this signal from its radio frequency carrier and furnishes the same to display 14. When utilized with the above model radiotelemetry transmitter 31, that portion of circuit to be carried by the patient (including the pH meter 15, waveform converter circuit 12 and ECG signal transmitter 31) weigh only slightly more than one pound and have a transmitting range of at least 75 feet. Thus, the patient is permitted to engage in most of his usual activities with minimal discomfort and interference, thereby producing a reflux pattern significantly more representative of that which is normally experienced.

Display 14 may be a continuous video display device, such as an oscilloscope, or a signal recorder, such as an X—Y plotter, where continuous and perhaps hard copy outputs are desired. Additionally, a frequency meter (not shown) could be provided to determine the number of voltage spikes per unit time and divide the same by the above noted proportionally constant, 20 herein, whereby display 14 may provide and record a direct readout of pH.

Operation of circuit 10 may begin after proper placement by trained medical personnel of the esophageal and reference electrodes 16 and 17, pH meter 15, waveform converter circuit 12 and ECG signal transmitter 31 upon the person of the patient by any suitable means (not relevant herein). Once connected, pH meter 15 continuously monitors the instantaneously measured esophageal pH and generates a D.C. signal whose voltage magnitude is proportional thereto. As explained hereinabove, this signal is converted to a signal whose waveform is similar to an ECG waveform, one of whose electrical properties is proportional to pH, and broadcast by ECG radiotelemetry system 31 ECG signal transmitter 31. This broadcast signal is received and demodulated so as to extract the ECG waveform signal containing the pH information. Display 14 provides an accurate time study of the patient's esophageal pH for use in diagnosis of gastroesophageal disease.

It should be appreciated that electrical properties other than frequency may be varied in proportion to instantaneous pH. For example, signal amplitude, impedance and phase could each be employed with suitable changes to waveform converter circuit 12. However, as previously noted, the characteristics of ECG signals make the use of frequency particularly appealing.

Inasmuch as the present invention is subject to many variations, modifications and changes in detail, a number of which have been expressly stated herein, it is intended that all matter described through this entire specification or shown in the accompanying drawings be interpreted as illustrative and not in a limiting sense. It should thus be evident that a device constructed according to the concept of the present invention, and reasonably equivalent thereto, will accomplish the objects of the present invention and other substantially improve the art of monitoring esophageal pH to obtain accurate reflux patterns.

We claim:

1. A circuit for radiotelemetry of an esophageal pH signal in an electrocardiogram (ECG) signal radiotelemetry system, comprising:
    means for monitoring esophageal pH and generating a signal proportional thereto;
    waveform converter means for receiving said signal from said means for monitoring esophageal pH and converting the same to a signal whose waveform is similar to an ECG waveform and one of whose electrical parameters is proportional to esophageal pH;
    transmitter means for receiving said converted signal from said waveform converter means and broadcasting the same upon a radio frequency carrier;
    receiver and demodulator means for receiving said broadcast signal and demodulating the same to obtain said converted signal similar to an ECG waveform; and,
    display means receiving said demodulated, converted signal whose waveform is similar to an ECG waveform and displaying indicia of esophageal pH.

2. A circuit, as set forth in claim 1, wherein said waveform converter means converts said signal from said means for monitoring esophageal pH to a signal whose frequency is proportional to esophageal pH.

3. A circuit for radiotelemetry of an esophageal pH signal in an electrocardiogram (ECG) signal radiotelemetry system, comprising: p1 means for monitoring esophageal pH and generating a D.C. signal whose voltage magnitude is proportional to esophageal pH;
    waveform converter means for receiving said D.C. signal from said means for monitoring esophageal pH and converting the same to a signal whose waveform is similar to an ECG waveform and one of whose electrical parameters is proportional to esophageal pH, said waveform converter means including voltage controlled oscillator (VCO) means for receiving said D.C. signal from said means for monitoring esophageal pH and generating a square-wave whose frequency is proportional to said voltage magnitude of said D.C. signal from said means for monitoring esophageal pH, and waveshaping filter means for receiving said square-wave from said VCO means and converting the same into a signal waveform similar to that of an ECG waveform;
    transmitter means for receiving said converted signal from said waveform converter means and broadcasting the same upon a radio frequency carrier;
    receiver and demodulator means for receiving said broadcast signal and demodulating the same to obtain said converted signal similar to an ECG waveform; and,
    display means receiving said demodulated, converted signal whose waveform is similar to an ECG waveform and displaying indicia of esophageal pH.

4. A circuit, as set forth in claim 3, wherein said waveform converter further includes divider means for receiving said square-wave and reducing said frequency of said square-wave to that compatible with the ECG signal radiotelemetry system.

5. A circuit, as set forth in claim 4, wherein said waveshaping filter means further includes R-C circuit means for producing a voltage spike with each change in polarity of said square-wave, diode means for eliminating said voltage spikes of one polarity, and output filter means to further define said voltage spikes of the remaining polarity.

6. A circuit, as set forth in claim 5, wherein said display means includes a signal recorder for providing a continuous, hard copy of said converted signal whose waveform is similar to an ECG waveform and whose frequency is proportional to esophageal pH.

7. A method for radiotelemetry of an esophageal pH signal in an electrocardiogram (ECG) signal radiotelemetry system, comprising the steps of:

monitoring esophageal pH including the step of generating a signal proportional to the instantaneously measured esophageal pH;

converting said signal proportional to the instantaneously measured esophageal pH to a signal whose waveform is similar to an ECG waveform and one of whose electrical parameters is proportional to esophageal pH;

broadcasting said converted signal upon a radio frequency carrier;

receiving and demodulating said broadcast signal to obtain said converted signal whose waveform is similar to an ECG waveform; and, displaying indicia of the instantaneous esophageal pH.

8. A method, as set forth in claim 7, wherein the step of monitoring esophageal pH further includes the steps of placing an esophageal pH electrode in a patient's esophagus, attaching a reference pH electrode to said patient's skin, and generating a D.C. signal whose voltage magnitude is proportional to said instantaneously measured esophageal pH.

9. A method for radiotelemetry of an esophageal pH signal in an elecatrocardiogram (ECG) signal radiotelemetry system, comprising the steps of:

monitoring esophageal pH including the steps of placing an esophageal pH electrode in a patient's esophagus, attaching a reference pH electrode to said patient's skin, and generating a D.C. signal whose voltage magnitude is proportional to said instantaneously measured esophageal pH;

converting said signal proportional to the instantaneously measured esophageal pH to a signal whose waveform is similar to an ECG waveform and one of whose electrical parameters is proportional to esophageal pH, said step of converting including the steps of generating a squarewave whose frequency is proportional to said voltage magnitude of said D.C. signal, and shaping said squarewave into a signal waveform similar to that of an ECG waveform;

broadcasting said converted signal upon a radio frequency carrier;

receiving and demodulating said broadcast signal to obtain said converted signal whose waveform is similar to an ECG waveform; and, displaying indicia of the instantaneous esophageal pH.

10. A method, as set forth in claim 9, wherein said step of converting further includes the step of reducing said frequency of said square-wave to that compatible with the ECG signal radiotelemetry system.

11. A method, as set forth in claim 10, wherein said step of shaping said square-wave includes the steps of producing a voltage spike of one polarity with each positive-going change in said square-wave and of an opposite polarity with each negative-going change in said square-wave, eliminating said voltage spikes of one said polarity, and filtering said voltage spikes of the remaining polarity.

12. A method, as set forth in claim 11, wherein said step of displaying includes the step of providing a continuous, hard-copy of said converted signal whose waveform is similar to an ECG waveform and whose frequency is proportional to esophageal pH.

* * * * *

UNITED STATES PATENT AND TRADEMARK OFFICE
CERTIFICATE OF CORRECTION

PATENT NO. : 4,326,535
DATED : April 27, 1982
INVENTOR(S) : Charles R. Steffel & Bruce C. Taylor It is certified that error appears in the above-identified patent and that said Letters Patent are hereby corrected as shown below:

Column 2, line 59, the word "instaneously" should read --instantaneously--.

Column 4, line 1, the word "to" (second occurrence) should read --the--.

Column 5, line 31, the word "proportionally" should read --proportionality--; line 62, the word "through" should read --throughout--.

Claim 3, Column 6, line 31, "pl" should be deleted.

Claim 9, Column 7, line 35, the word "elecatrocardiogram" should read --electrocardiogram--.

Claim 9, Column 8, line 9, the word "squarewave" should read --square-wave--.

Claim 9, Column 8, line 11, the word "squarewave" should read --square-wave--.

Signed and Sealed this

Second Day of November 1982

[SEAL]

Attest:

GERALD J. MOSSINGHOFF

Attesting Officer   Commissioner of Patents and Trademarks